United States Patent
Wood et al.

[11] Patent Number: 5,994,067
[45] Date of Patent: Nov. 30, 1999

[54] METHOD AND KIT FOR RAPID DETECTION OF TOXINS AND BACTERIA

[75] Inventors: Sheila J. Wood; Robert J. Sydiskis, both of Abingdon, Md.

[73] Assignee: The United States of America as represented by the Secretary of the Army, Washington, D.C.

[21] Appl. No.: 08/745,541

[22] Filed: Nov. 12, 1996

Related U.S. Application Data

[60] Provisional application No. 60/006,725, Nov. 14, 1995.

[51] Int. Cl.$^6$ .................................................. C12Q 1/68
[52] U.S. Cl. .............................................. 435/6; 435/7.1
[58] Field of Search ........................................ 435/6, 7.1

[56] References Cited

U.S. PATENT DOCUMENTS

| | | | |
|---|---|---|---|
| H1398 | 1/1995 | Campbell | 435/6 |
| 4,343,782 | 8/1982 | Shapiro | 424/3 |
| 5,183,740 | 2/1993 | Ligler et al. | 435/7.32 |

(List continued on next page.)

OTHER PUBLICATIONS

Boman, HG et al, Infect. & Immun, Jul., vol. 61 (7), pp. 2978–2984, 1993.
Piers, KL et al, Molecular Microbiolo, vol. 12(6) pp. 951–958, (Jun.), 1994.
Piers, KL et al, Antimicrobial Agents & Chemotherapy, Oct. 1994, pp. 2311–2316, vol. 38(10), 1994.
Lalande, ME et al, Proc. Natl. Acad, Sci(USA), Jan., vol. 78(1), pp. 363–7, 1981.
Terzieva, S et al, Applied & Environm. Microbiol. vol. 62(7), pp. 2264–2272, 1996.
Kim, Sang–Nyun, vol. 56/11–B of Dissertation Abstracts International, p. 5922, 125 pages, 1995.
Benzoechea, JA et al, Infect. & Immun., vol. 64 #12, (Dec.), pp. 4891–4899, 1996.
Langsrud, S et al., J. of Applied Bacteriol, vol. 81 pp. 411–418, (Feb.), 1996.
Christensen, B et al, Jul. 1988, Proc. Nat'l Acad. Sci(USA), vol. 85(14), pp. 5072–6(abs.).
Peasek, J et al, J. of Photochem. & Photobiol. B–Bio. 1996, vol. 33(2), Apr., pp. 101–124.

(List continued on next page.)

*Primary Examiner*—James C. Housel
*Assistant Examiner*—Ginny Allen Portner
*Attorney, Agent, or Firm*—Ulysses John Biffoni

[57] ABSTRACT

In one aspect of the invention there is described a method of detecting the presence of toxins, which may traverse bacterial membranes in some manner, in environmental samples using an indicator bacteria such as *E. coli* K-12 and a fluorescent signal. The method includes:

(a) obtaining a positive control signal by placing an indicator bacteria strain such as *E. coli* K-12 and a bactericidal peptide such as a cecropin in a suitable buffer containing a fluorescent marker for bacterial DNA such as SYTOX;

(b) obtaining a negative control signal by placing only the indicator bacteria strain in the buffer containing the fluorescent marker for bacterial DNA;

(c) obtaining a test signal by combining an environmental test sample with the indicator bacteria strain and the fluorescent marker for bacterial DNA in the buffer; and (d) comparing the signal generated by the test sample to that obtained for the negative control. The presence of a toxin in the test sample is indicated when the test signal is greater than the signal provided by the negative control.

Also described herein is a method of detecting the presence of bacteria in environmental samples using fluorescent markers and bactericidal peptides which penetrate or allow penetration of substances into bacteria, and kits for carrying out the above methods.

19 Claims, 9 Drawing Sheets

U.S. PATENT DOCUMENTS

| | | | |
|---|---|---|---|
| 5,314,805 | 5/1994 | Haugland et al. | 435/29 |
| 5,321,130 | 6/1994 | Yue et al. | 536/23.1 |
| 5,354,654 | 10/1994 | Ligler et al. | 435/5 |
| 5,358,690 | 10/1994 | Guirguis | 422/58 |
| 5,360,819 | 11/1994 | Giese | 514/538 |
| 5,366,881 | 11/1994 | Singh et al. | 435/177 |
| 5,437,978 | 8/1995 | Ubukata et al. | 435/6 |
| 5,441,934 | 8/1995 | Krapcho et al. | 514/12 |
| 5,474,910 | 12/1995 | Alfano | 435/34 |
| 5,496,700 | 3/1996 | Ligler et al. | 435/7.1 |
| 5,519,115 | 5/1996 | Mapellli et al. | 530/324 |
| 5,534,416 | 7/1996 | Millard et al. | 436/34 |
| 5,545,535 | 8/1996 | Roth et al. | 435/34 |
| 5,593,866 | 1/1997 | Hancock et al. | 435/69.2 |
| 5,696,157 | 12/1997 | Wang et al. | 514/457 |
| 5,714,467 | 2/1998 | Boman et al. | 514/12 |

OTHER PUBLICATIONS

Duclohier, H, Toxicology, Feb. 28, 1994, vol. 87(1–3), pp. 175–88.

Moore, AJ et al, J. Antimicrob. Chemother. Jun. 1996, vol. 37(6), pp. 1077–1089.

Millard, P.J. et al, Abstracts Gen. Meeb. Am. Soc. Microbiol., May 21–25, 1995, vol. 95(0), pp. 477,Q–440.

Porter, J. et al, J. App. Bacteriol., 1995, vol. 79(4), pp. 399–408.

Vaara, M., Microbiol. Rev., Sep. 1992, vol. 56(3), pp. 395–411.

METHOD AND KIT FOR RAPID DETECTION OF TOXINS AND BACTERIA

This nonprovisional application is entitled to the benefits of provisional application Ser. No. 60/006,725 filed Nov. 14, 1995.

GOVERNMENT INTEREST

The invention described herein may be manufactured, licensed, and used by or for the U.S. Government.

BACKGROUND OF THE INVENTION

1. Field of the Invention

The present invention relates to methods of rapidly detecting the presence of toxins in a given environment. In particular, the invention relates to toxin detection methods using bacteria stained with a fluorescent indicator. The invention also relates to methods of detecting bacteria using fluorescent indicators.

2. Description of the Related Art

Recently, governments have become increasingly interested in identifying and controlling the biological warfare agents (BWA's) which have been developed and stockpiled by several nations. These agents are highly dangerous and extreme caution mIst be used in the handling of these agents. In the event that these agents are deployed, part of the initial defense includes the rapid and accurate detection of the agents. Currently available military systems for detecting and identifying bacteria and/or toxins are laboratory based, requiring sophisticated and expensive equipment. Once such system is essentially a mobile sheltered laboratory designed to collect and analyze biological samples in the field. However, such systems are expensive, limited in number, and require significant laboratory time and trained personnel in order to positively identify biological warfare agents including toxins. The ability to rapidly and inexpensively detect the presence of toxins in field samples on-site remains an unmet need. Moreover, the demand for methods and kits capable of rapidly detecting toxins has applications beyond those of the military such as pharmaceutical, medical, and food industries.

In view of the advantages of rapidly and accurately identifying the presence of BWA's, toxins and associated by-products, and further in view of the need to address the shortcomings associated with currently available detection methods, there is still a need for new and improved detection methods and kits. In particular, there remains a need for rapidly and accurately detecting sub-microgram quantities of toxins, BWA's and their precursors and related degradation byproducts. The present invention addresses these need.

SUMMARY OF THE INVENTION

In view of the foregoing, it is therefore an object of the present invention to provide an improved method for rapidly detecting toxins and/or bacteria in a given environmental sample.

It is a further object of the invention to provide a method for rapidly detecting toxins in a sample by measuring the effect or lack of effect on a combination of a bacteria and fluorescent indicator.

In one aspect of the invention, these and other objects of the invention are achieved by a method of detecting the presence of toxins, particularly toxins which may traverse the bacterial membrane in some manner, in environmental samples using an indicator bacteria (such as $E.$ $coli$ K-12) and a fluorescent signal, which comprises:

(a) obtaining a positive control signal by placing an indicator bacteria strain, such as $E.$ $coli$ K-12, and a bactericidal peptide such as a cecropin in a suitable buffer containing a fluorescent marker for bacterial DNA such as SYTOX;

(b) obtaining a negative control signal by placing only the indicator bacteria strain in the buffer containing the fluorescent marker for bacterial DNA;

(c) obtaining a test signal by combining an environmental sample with the indicator bacteria strain and the fluorescent marker for bacterial DNA in the buffer; and (d) comparing the signal generated by the test sample to that obtained for the negative control. The presence of a toxin in the test sample is indicated when the signal is greater than the signal provided by the negative control.

In a second embodiment of the invention, there is provided a method of detecting the presence of bacteria in environmental samples. The method includes using peptides which preferentially bind specifically to bacterial membranes and/or bacterial cell walls and penetrate or allow penetration of substances into bacteria. The method thus comprises:

(a) obtaining a positive control signal by combining an indicator bacteria strain such as $E$ $coli$ K-12, a fluorescent marker for bacterial DNA such as SYTOX and a bactericidal peptide such as cecropin in a suitable buffer;

(b) obtaining a negative control signal by combining the indicator bacteria strain with the fluorescent marker for bacterial DNA in the buffer, (no bactericidal peptide is included);

(c) obtaining a test signal by placing an environmental sample in a suitable buffer along with the fluorescent marker for bacterial DNA and a bactericidal peptide; and (d) comparing the signal generated by the test sample to the signal obtained for the negative control. The presence of bacteria in the test sample is indicated when the test fluorescent signal is greater than the signal of the negative control.

In each of the foregoing embodiments, it will be understood that the signals generated in each step of the methods are measured by a suitable fluorescent measurement apparatus and that the signals are generated as a result of placing the individual reagents for each step of the methods in separate vessels such as beakers or test tubes.

In still another aspect of the invention there are provided kits for carrying out the methods described above. The kits include all necessary reagents and vessels for detecting the presence of toxins or bacteria in an environmental sample. For example, the kits include all necessary components for establishing a positive control and a negative control as well as sample vessels for holding the environmental samples. Accordingly, the kits contain a sufficient amount of lyophilized indicator bacteria, such as $E.$ $coli$ K-12 and its strains which are readily available to the public from the American Type Culture Collection (ATCC), Rockville, Md. (for use in the positive, negative and test sample vessels); a sufficient amount of the fluorescent marker for bacterial DNA, for example SYTOX which is available from Molecular Probes Inc., Eugene, Oreg., a new class of fluorescent unsymmetrical cyanine nucleic acid stains, lyophilized bactericidal peptide such as cecropin; and sufficient amounts of buffer. The kit can also comprise a suitable container or other suitable means for holding and transporting a plurality of vessels or tubes which contain the individual reagents as well as tubes to be used for carrying out the individual signal assays. For example, one kit in accordance with th, invention includes one tube containing the lyophilized bacteria, one tube containing the SYTOX, one tube containing the buffer solution and a still further tube containing the lyophilized cecropin, either alone or in combination with a fluorescent or luminescent indicator. After collecting an environmental sample, detection of the toxins or bacteria via signals is effected with a suitable fluorescent measurement apparatus such as a Cytofluor 2300, available from Millipore Corp., Bedford, Mass. The fluorescent measurement apparatus is optionally included in the kit described herein. It will be understood by those of ordinary skill in the art that there are alternative fluorescent measurement apparatus which can be used in the methods described herein.

The advantages of the present invention include the fact that it provides a rapid detection system for toxins using bacteria stained with a fluorescent indicator. Another advantage is that the kits allow the method to be carried out in field locations.

DETAILED DESCRIPTION OF THE PREFERRED EMBODIMENT

In one aspect of the present invention, the present invention includes a method of detecting the presence of toxins in environmental samples using an indicator bacteria (such as *E. coli* K-12) and a fluorescent signal, which comprises:

(a) obtaining a positive control signal by placing an indicator bacteria strain and a bactericidal peptide such as a cecropin in a suitable buffer containing a fluorescent marker for bacterial DNA such as SYTOX;

(b) obtaining a negative control signal by placing only the indicator bacteria strain in a buffer containing the fluorescent marker for bacterial DNA;

(c) obtaining a test signal by combining an environmental sample with the indicator bacterial strain and the fluorescent marker for bacterial DNA indicator in the buffer; and (d) comparing the signal generated by the test sample to the signal obtained for the negative control. The presence of a toxin in the test sample is indicated when the test sample signal is greater than that of the negative control. As an alternative to the method described above, water can be used in place of the buffer to burst the bacteria in the step for obtaining a positive control.

Preferably, the indicator bacteria strain used in carrying out the method is an *Escherichia coli* such as *Escherichia coli* K-12, including strains LE392, Y1083, JM109, MC1061 and C600 which are readily available from ATCC. *E. coli* K12 is a standard organism used in microbiology laboratories. It is used often in experiments which transfer genetic elements into the organism. It lacks the O-antigen domain but this does not hamper growth in any way. The O-antigen domain is presumed to be important for establishing infections in mammalian organisms. The two other domains in the cell wall remain intact. They consist of the core region (sugar residues) and the lipid A. moiety. For purposes of the present invention, however, the bacteria is desirable for its ability to allow indication of entry by the fluorescent indicator. The substances tested (i.e. cecropins) do not "burst" the membranes but instead form a pore or hole through which they can enter, much the same as calcium ion channels. Bacterial cell membranes are difficult to disrupt as long as they are placed in buffered saline. Thus, it is preferred that all samples used in carrying out the methods described herein are placed in such a buffer. The sample would be centrifuged or filtered to remove debris. Bacteria occur naturally in the soil, so they can survive under a variety of environmental extremes. *E. coli* K-12 organisms are also advantageous since they can be lyophilized or frozen and stored for years without changes occurring. Thus, kits, as describe above, can be prepared in accordance with the present invention to contain sufficient *E. coli* and testing apparatus so that field tests, for example, can be carried out after the *E. coli* has been "reconstituted". Alternatively, the indicator bacteria used in the method of the present invention can be any bacteria known to be sensitive to cecropin bactericides.

In the practice of the invention, the test for presence of toxins is designed to use a bacteria as the indicator strain and the toxin as the penetrator of the (bacterial) membrane. For example, freeze-dried *E. coli* K-12 is reconstituted in buffer and a buffered sample added to it prior to monitoring. This would provide a stable environment for the reaction to take place.

The methods of the present invention preferably include carrning out the test in a suitable buffer. Most biological tests require conditions around pH 7.0. High salt or high ionic strength are rarely allowed in any biological evaluation. Therefore, the samples and the bacteria are suspended in suitable buffers such as NaCl-HEPES. Air samplers can also be used to collect samples from air and can be outfitted with any buffer one prefers to use using techniques well known to those of ordinary skill in the art. Any solvent or buffer system could be used as long as both negative and positive controls are used.

Negative and positive controls provide windows of usefulness for the user and account for any interference. In other words, the fluorescent marker for bacterial DNA (i.e. SYTOX) uptake into the test bacterium is measured and compared to SYTOX uptake in the absence of toxin and SYTOX uptake in the presence of a control toxin. Signals above background (or absence of toxin) can be considered positive if they are preferably about twice as high as the negative control.

The negative control consists of a sample of indicator bacteria taken directly from the growing culture, then diluted in buffer containing SYTOX or other suitable fluorescent marker. The SYTOX or fluorescent marker uptake is a measure of dead cell background. This is a baseline reading. The same dilution of bacteria, i.e. *E. coli* K-12 and fluorescent marker i.e. SYTOX containing toxin (test) measures dead bacteria over and above the normally occurring dead bacteria (of which there are very few). One useful and preferred measure for indicating the positive presence of toxins using the bacterial-based indicator described herein is when the test signal is about three times greater than the negative control. About a two-fold or greater difference in signals can also be used. A positive control for the methods can be water or toxins such as cecrepins to cause permeations in most of the bacteria present, so that reads will be higher than the test reads. Positive controls tell the user if the fluorescence upon binding to the bacterial DNA is working adequately.

The fluorescent or luminescent marker agent used in the processes of the present invention is preferably selected from among fluorescent agents which have a relatively high affinity for nucleic acids such as SYTOX. Alternatively, a non-limiting list of fluorescent agents include materials such as LIVE/DEAD BacLight kits or SYTOX or any fluorescent markers which fluoresce when bound to bacterial DNA such as acridine orange, DAPI, Hoescht 33342 and dihydroethidium. All of the foregoing stains are available from Molecular Probes, Inc. Eugene, Oreg.

The method of the invention is useful in detecting toxins such as, for example, *Escherichia coli* heat-labile enterotoxin, *Escerichia coli* heat stable enterotoxin, cholera toxin, adenylate cyclase activating polypeptide, staphylococcal enterotoxin, Ricin A chain, conotoxin, charybdotoxin and sarafotoxin.

In another aspect of the invention, there is provided a method of detecting the presence of bacteria in environmental samples using peptides which preferentially bind specifically to bacterial membranes and/or bacterial cell walls and penetrate or allow penetration of substances into bacteria, which comprises:

(a) obtaining a positive control signal by combining an indicator bacteria strain (i.e. *E. coli* K-12), a fluorescent marker for bacterial DNA such as SYTOX, and a bactericidal peptide such as cecropin in a suitable buffer;

(b) obtaining a negative control signal by combining the indicator bacteria strain with the fluorescent marker for bacterial DNA in the buffer, (no bactericidal peptide is included);

(c) obtaining a test signal by placing an environmental sample in a suitable buffer along with the fluorescent marker for bacterial DNA and bactericidal peptide; and (d) comparing the signal generated by the test sample to the signal obtained for from the negative control. The presence of bacterial in the test sample is indicated when the fluorescent signal is greater than that of the negative control.

As was the case with the first embodiment described above, the indicator bacteria is preferably *Escherichia coli* and more preferably *Escherichia coli* K-12 selected from strains LE392, Y1083, JM109, MC1061 and C600. In this aspect of the invention, the fluorescent marker is also preferably SYTOX. Examples of bacteria which may be detected include, without limitation, *Escherichia coli* other than K-12, non-toxin A producing *Vibrio cholera* and *Pseudomonas aerugenosa*.

1. OVERVIEW OF THE METHODS

The procedures described below set forth preferred embodiments of the invention and serve to illustrate preferred modes of carrying out the invention.

The rationale for using bacteria in the methods described herein are based at least in part on properties of a unique antibiotic called cecropin. Cecropins are small basic peptides, 30–35 amino acids in length, and have been shown to have antibacterial properties. They have been isolated from insects and the intestines of pigs. Cecropins have marked antibacterial activities against a variety of bacteria tested including a variety of pathogenic gram-positive and gram-negative bacteria, fungi, protozoa and enveloped viruses. Cecropin B, isolated from insects, is active on wild-type enteric bacteria and their lipopolysaccharide/lipid A mutants that have defective outer membranes, as exemplified by K-12 strains of *E. coli*. The mode of action of the cecropin peptides involves pore formation at the cytoplasmic membrane, and their action resembles the activity of quaternary detergents.

In developing the methods of the present invention and the protocol for the toxin detection system, the above observations on the mode of action of the cecropins formed the rationale for the methods. It was reasoned that if a toxin could also damage the membrane of a bacterium sufficiently to allow the penetration of a fluorescent marker, the fluorescent marker could be detected in a fluorimeter. The prototypical fluorescent marker chosen for this study was SYTOX (Molecular Probes, Inc. Eugene Oreg.). This is a green fluorescent dead cell stain with a high-affinity for nucleic acids. It easily penetrates both gram-positive and gram-negative bacteria with compromised plasma membranes, and yet is completely excluded from live cells. Once attached to the cellular DNA the SYTOX fluorescence is enhanced 1000-fold, producing a bright green fluorescent signal when excited at any 470–490 nm light source. As pointed out above, however, alternatives can be used in carrying out the methods described herein.

The concept of the invention therefore is a relatively straight forward one. A bacterium such as a mutant strain of *E. coli* (K-12) with a compromised plasma membrane is mixed with a fluorescent marker such as SYTOX and a test sample containing a toxin. If the toxin further damages the plasma membrane of the bacteria, the membrane becomes permeable enough to allow the uptake of the SYTOX into the cell. SYTOX then binds to the DNA of the bacteria and can be detected as a fluorescent signal. The amount of fluorescence is proportional to the amount of SYTOX taken up by the bacteria and bound to its DNA. A significant increase in signal over the appropriate controls indicates that the toxin was present in the sample and therefore detectable in this system.

2. MATERIALS AND METHODS 2.1 Organisms Used.

*Escherichia coli* K-12 strains LE 392, Y1083, JM 109, MC 1061, and C 600 were clone purified on Tryptocase Soy Agar (Becton Dickinson, Cockeysville, Md.). Strain C 600 was preferred based on preliminary growth studies. Strain C 600 was routinely grown in Nutrient Broth (NB) (Scott Labs, Fiskville, R.I.) on a shaker overnight at rocm temperature. Optical density reading were taken and, based on a standard O.D. versus Colony Forming Units graph, the number of organisms were determined and diluted initially to a starting concentration in all experiments described below to $2 \times 10^8$ CFU/ml. All five strains described above were sub-cultured weekly on Tryptocase Soy Agar plates from single colonies 2.2 Test Materials, Solutions and Buffers.

SYTOX DNA dead cell stain was obtained from Molecular Probes, Inc. (Eugene, Oreg.). It was diluted in water or NaCl-HEPES buffer, pH 7.4 to an initial working concentration of 50 uM. The following test materials were obtained from Sigma Chemical Co. (St. Louis, Mo.): Cecropin A, B, and P1; E. coli heat-labile enterotoxin; E. coli heat-stable enterotoxin; Cholera toxin; adenylate cyclase activating polypeptide; staphylococcal enterotoxin; Ricin A and B chains; conotoxin; charybdotoxin, and sarafotoxin.

2.3 Assay Procedure.

Assays of test materials were conducted as follows. K-12 strain C 600 was grown and diluted as described above and further diluted in NaCl-HEPES buffer to a final concentration of $2 \times 10^8$ CFU/ml. Test materials were reconstitued according to manufacturer's directions and mixed with the tubes containing the bacteria and SYTOX. Using 96-well flat bottom plates (Corning, Corning, N.Y.) horizontal wells were filled with 200 ul of the following: Indicator bacteria, cecropin, and SYTOX in buffer (positive control); indicator bacteria, buffer and 0.5 uM SYTOX (negative control); and decreasing concentrations of test material in buffer, indicator bacteria plus SYTOX (0.5 uM) in the other rows of wells. The plates were placed in a Cytofluor 2300 Fluorescence Measurement System (Millipore Corp., Bedford, Mass.) and the amount of fluorescence emitted from the SYTOX bound to the DNA of dead bacteria was read in the instrument using an excitation filter of 485+−20 nanometer wavelengths and an emission filter of 530+−25 nanometer wavelength. The amount of fluorescence was measured by a photomultiplier tube and recorded as a printout of a series of numbers for each well; the higher the number the higher the amount of fluorescence detected. It is important to keep in mind that, when comparing the test toxin data to the controls, the same suspension of E. coli K-12 should be separated and used for test and controls.

3. EXAMPLES

The following non-limiting examples serve to illustrate the invention.

3.1. Cecropins

Figure 1:
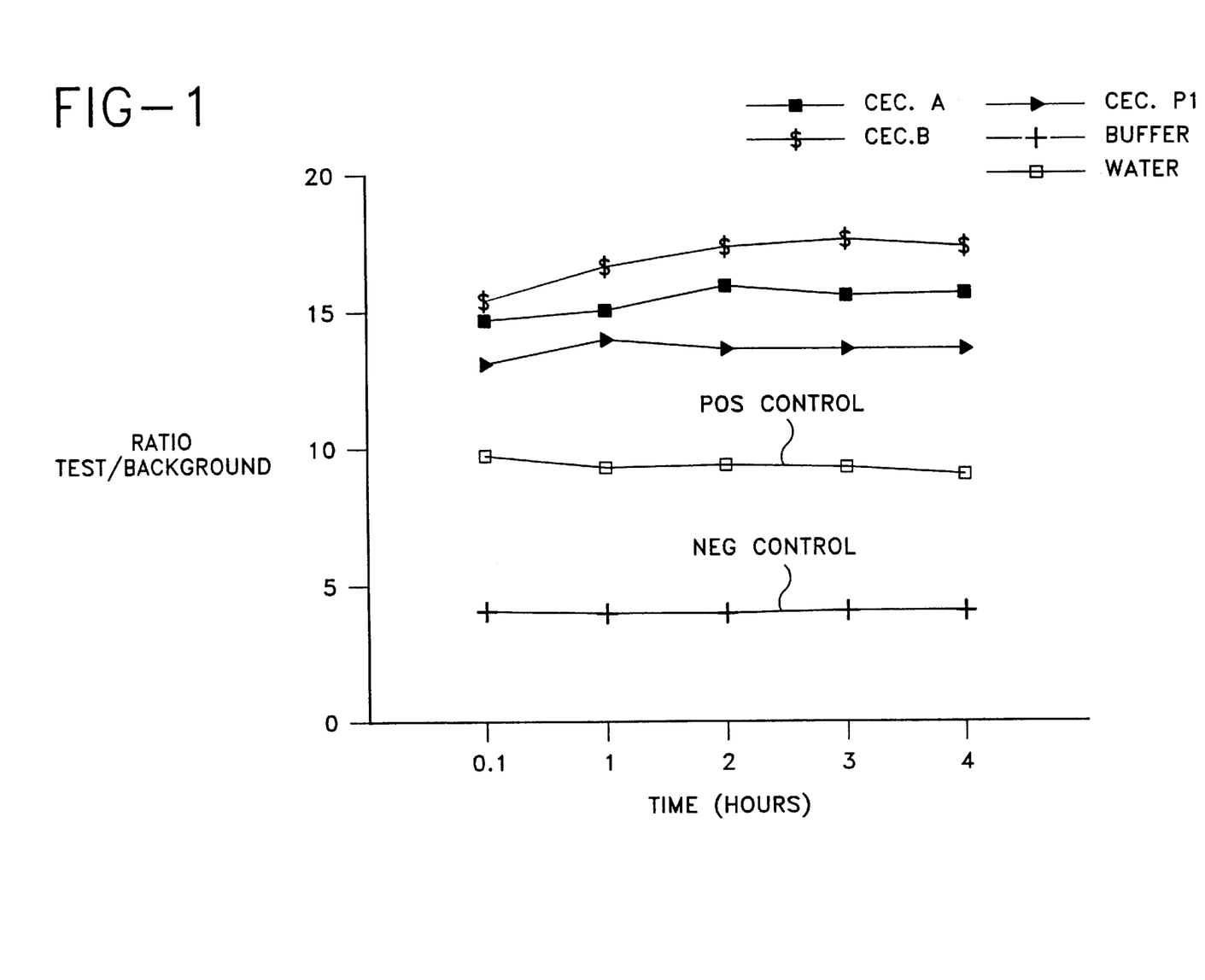
FIG. 1 is a graph illustrating fluorescence uptake by *E. coli* in the presence of cecropin A, B, and P1 using a process in accordance with the present invention.

Cecropin A, B, and P1 were diluted and tested at various concentrations from 0.1 to 10 ug/ml and tested in the manner described above with the appropriate negative and positive controls. The results are shown in FIG. 1. As seen, all three cecropins showed a positive SYTOX uptake at 10 ug/ml within the first time frame tested (0.1 fur). The negative buffer control showed a low level of SYTOX uptake which remained steady throughout the 4 hr test period. The positive control demonstrated that the system was working as intended with an increase in SYTOX uptake over the negative control. These controls were used throughout the remainder of the study and the data is presented in each subsequent Figure without further comment.

3.2 E. coli Enterotoxins

Heat stable E. coli enterotoxin and heat labile E. coli enterotoxin were each reconstituted according to the manufacturers recommendation and each was placed in a test solution (buffer, indicator bacteria E. coli K-12, and SYTOX). They were tested as described and both enterotoxins tested positive, compared with their appropriate controls, as quickly as the test wells could be assayed (0 hr time). The most significant measurements were at zero time in the case of these toxins. The levels of fluorescence had decreased to control levels at 5 hours.

3.3 Cholera Toxin

Figure 2:
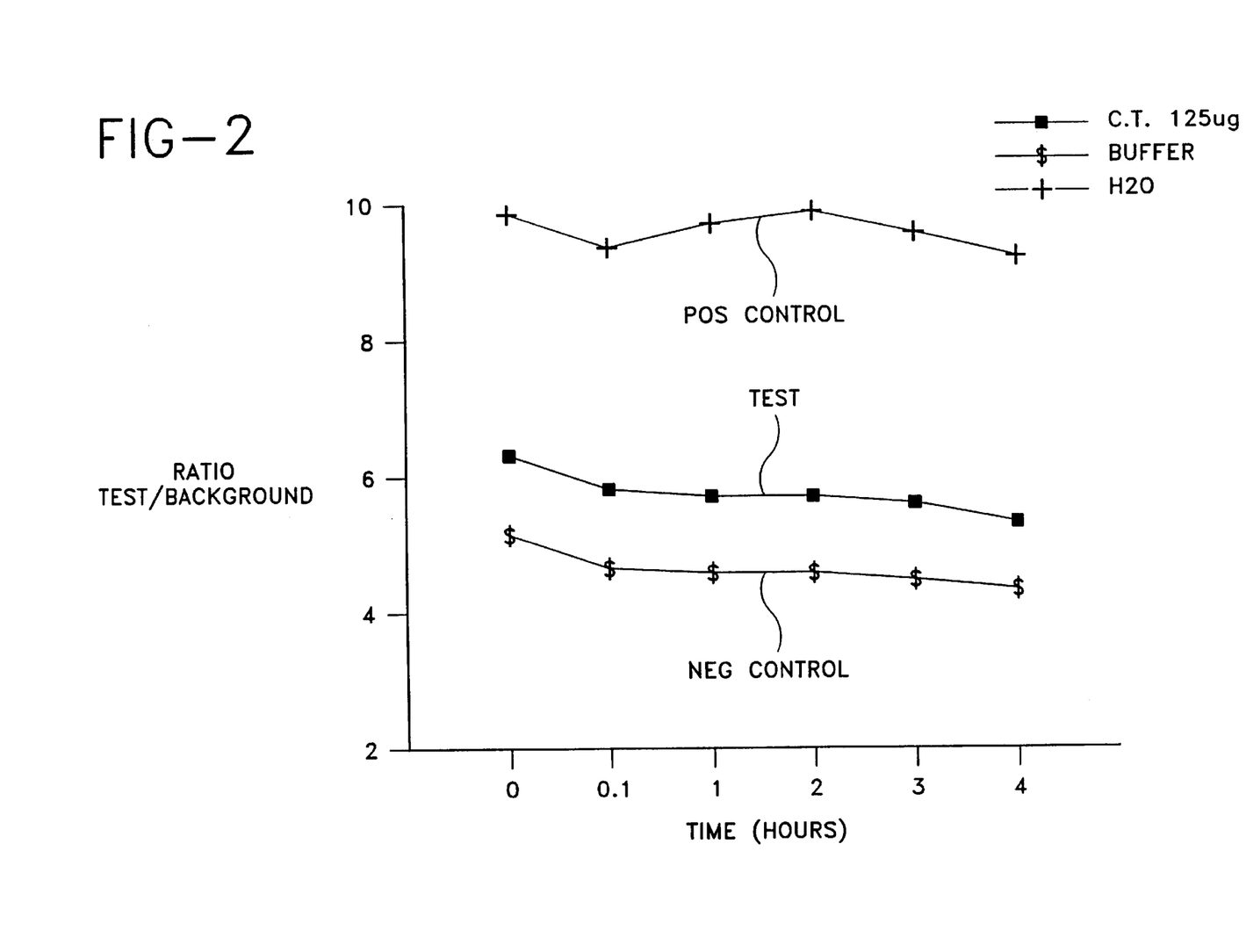
FIG. 2 is a graph illustrating fluorescence uptake by *E. coli* in the presence of cholera toxin.

Cholera toxin was reconstituted and tested as described. As seen in FIG. 2, the cholera toxin test was positive at 0 time through 4 hr well above the positive control.

3.4 Adenylate Cyclase Activating Polypeptide

Figure 3:
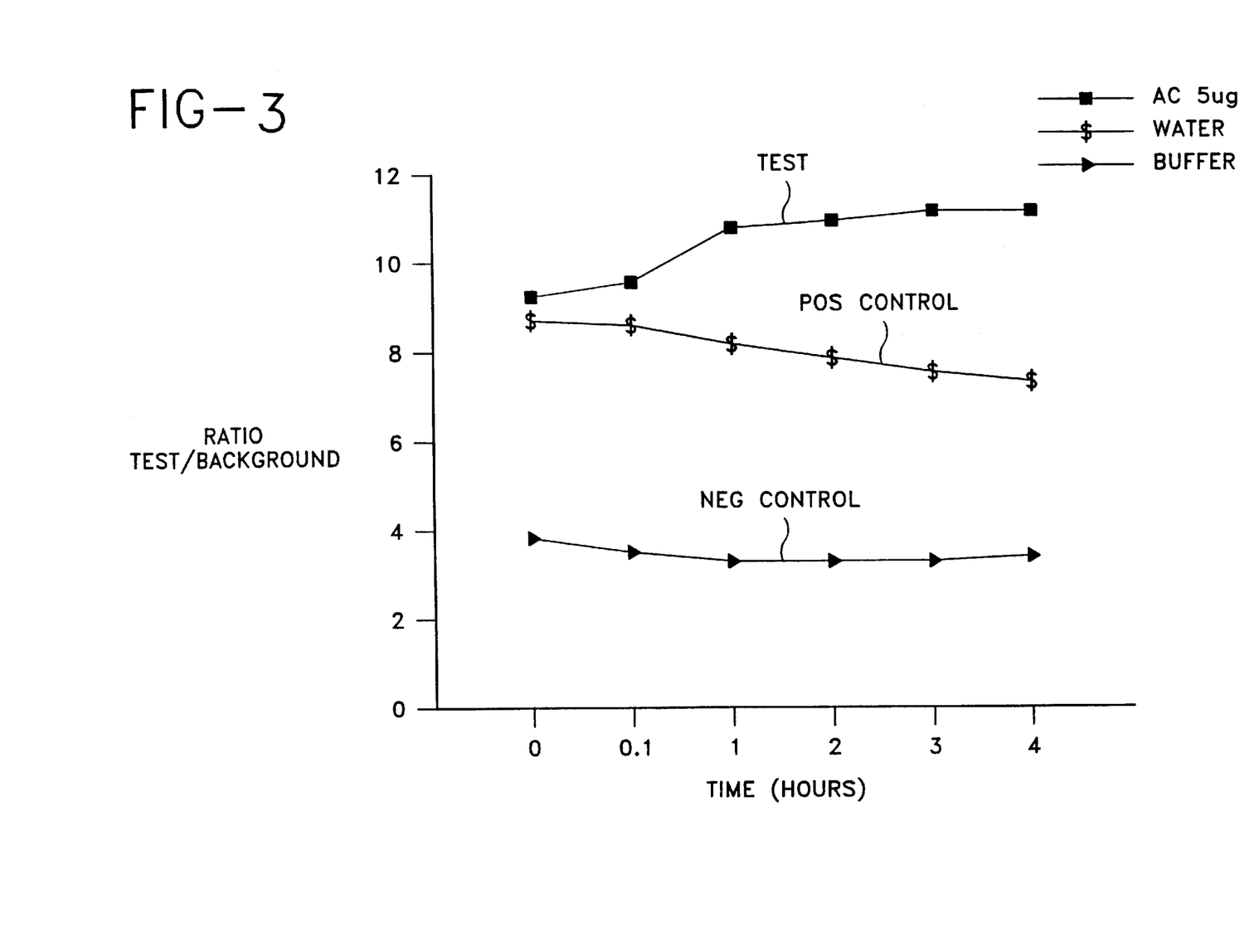
FIG. 3 is a graph illustrating fluorescence uptake by *E. coli* in the presence of adenylate cyclase activating peptide using a process in accordance with the present invention.

Since cholera toxin tested positive, it became of interest to see if adenylate cyclase activating polypeptide (ACAP) would also test positive in this assay. This enzyme has the same mode of action on cells as cholera toxin, activating a cascade effect resulting in the ultimate rapid loss of fluids from the cells identical to cholera toxin action. ACAP was diluted and E. coli K-12 bacteria assayed for SYTOX uptake. FIG. 3 shows that ACAP also resulted in an increase in SYTOX uptake by bacteria from 0 through 4 hr.

3.5 Staphylococcal Enterotoxin

Figure 4:
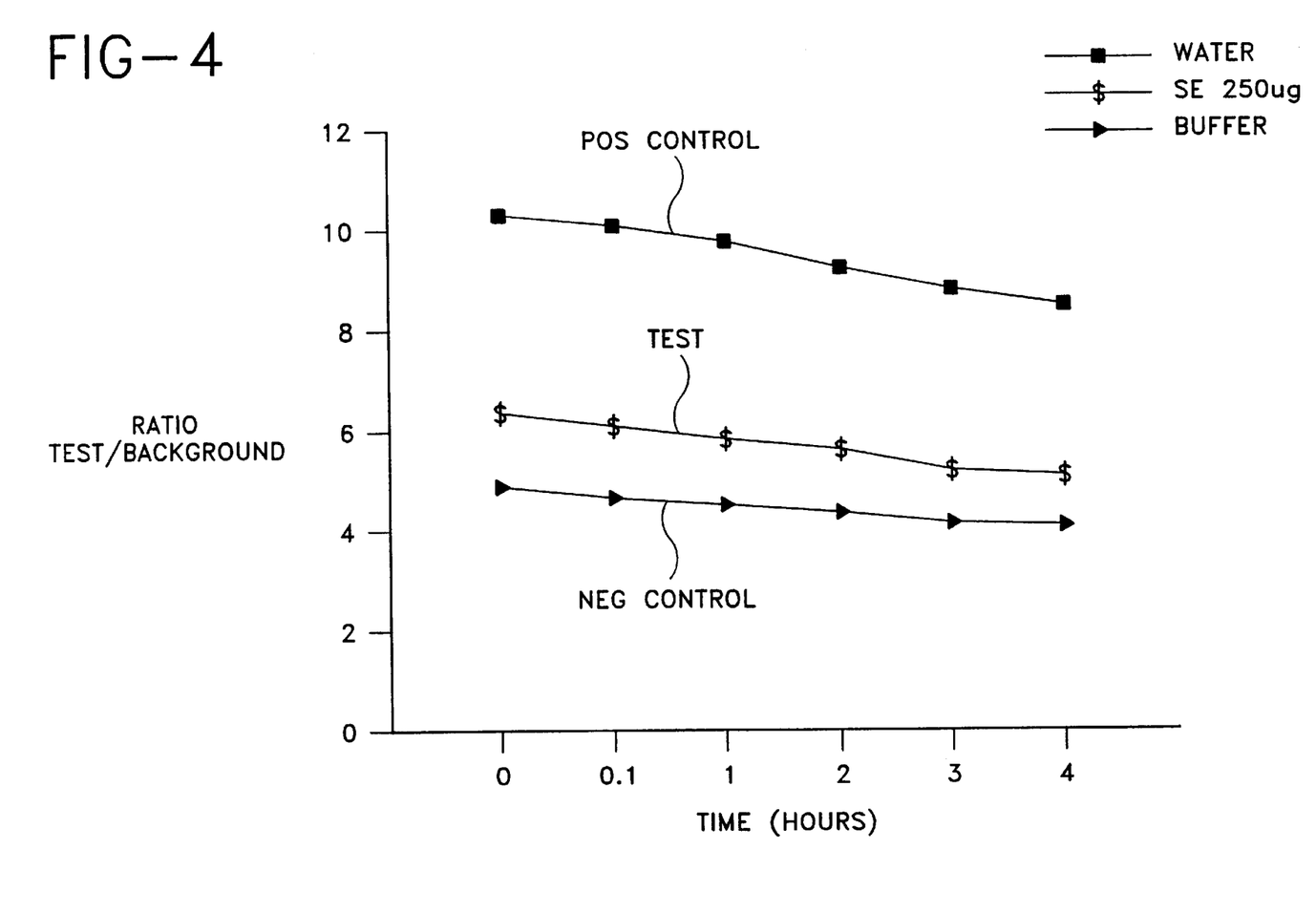
FIG. 4 is a graph illustrating fluorescence uptake by *E. coli* in the presence of staphylococcal enterotoxin using a process in accordance with the present invention.

Staphylococcal enterotoxin was reconstituted and diluted in buffer and tested as described. The results show that this enterotoxin could be readily detected at 0 time through 4 hr as shown in FIG. 4.

3.6 Ricin A and B Chain

Figure 5A:
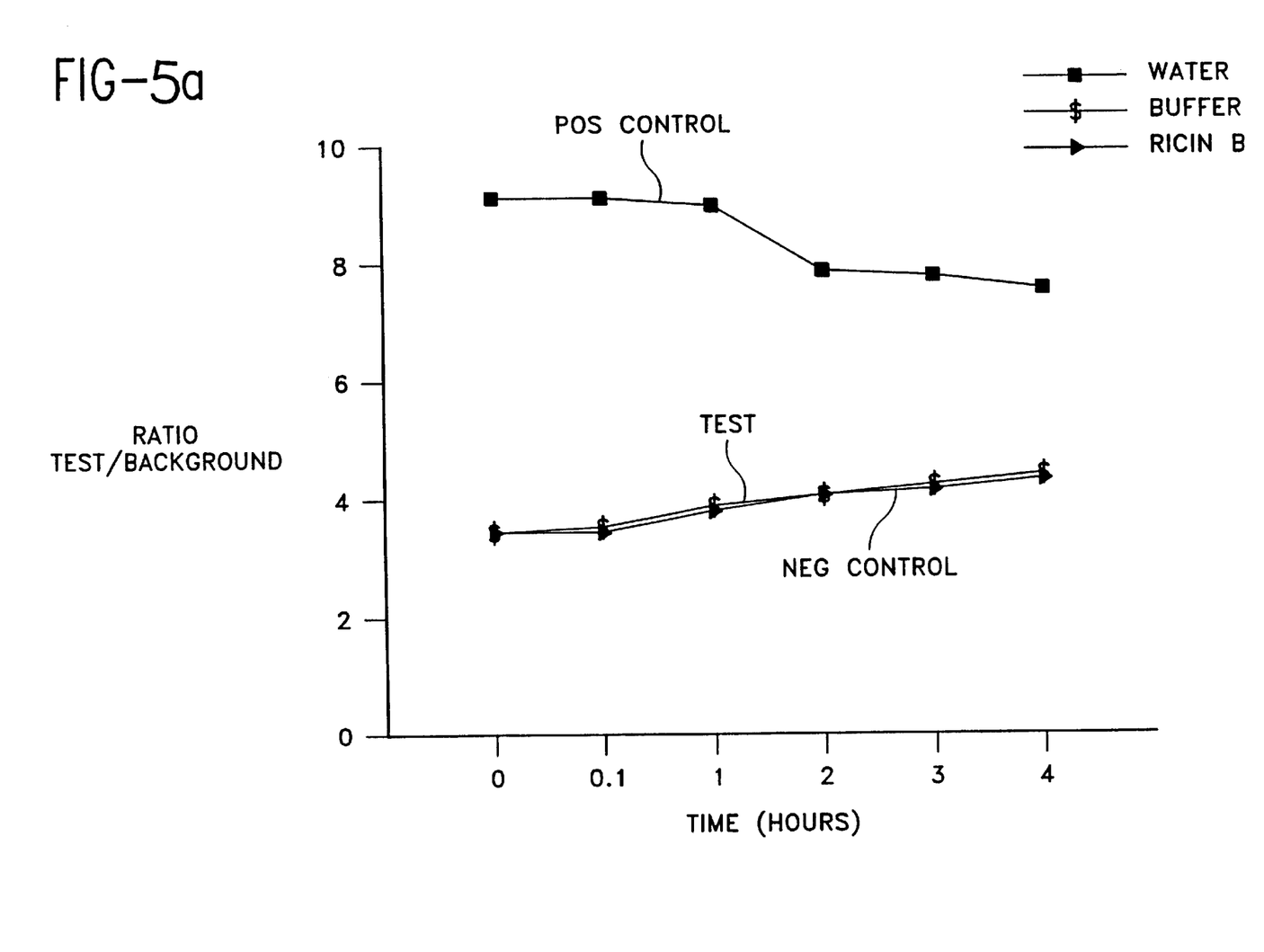
FIG. 5a is a graph illustrating no fluorescence uptake by *E. coli* in the presence of Ricin B chain using a process in accordance with the present invention.

Ricin B chain serves as the receptor for the complete Ricin molecule and alone is not toxic. Ricin B chain was diluted in buffer and tested. As expected, the results (FIG. 5a) showed no increase in SYTOX uptake in the tests performed.

Figure 5B:
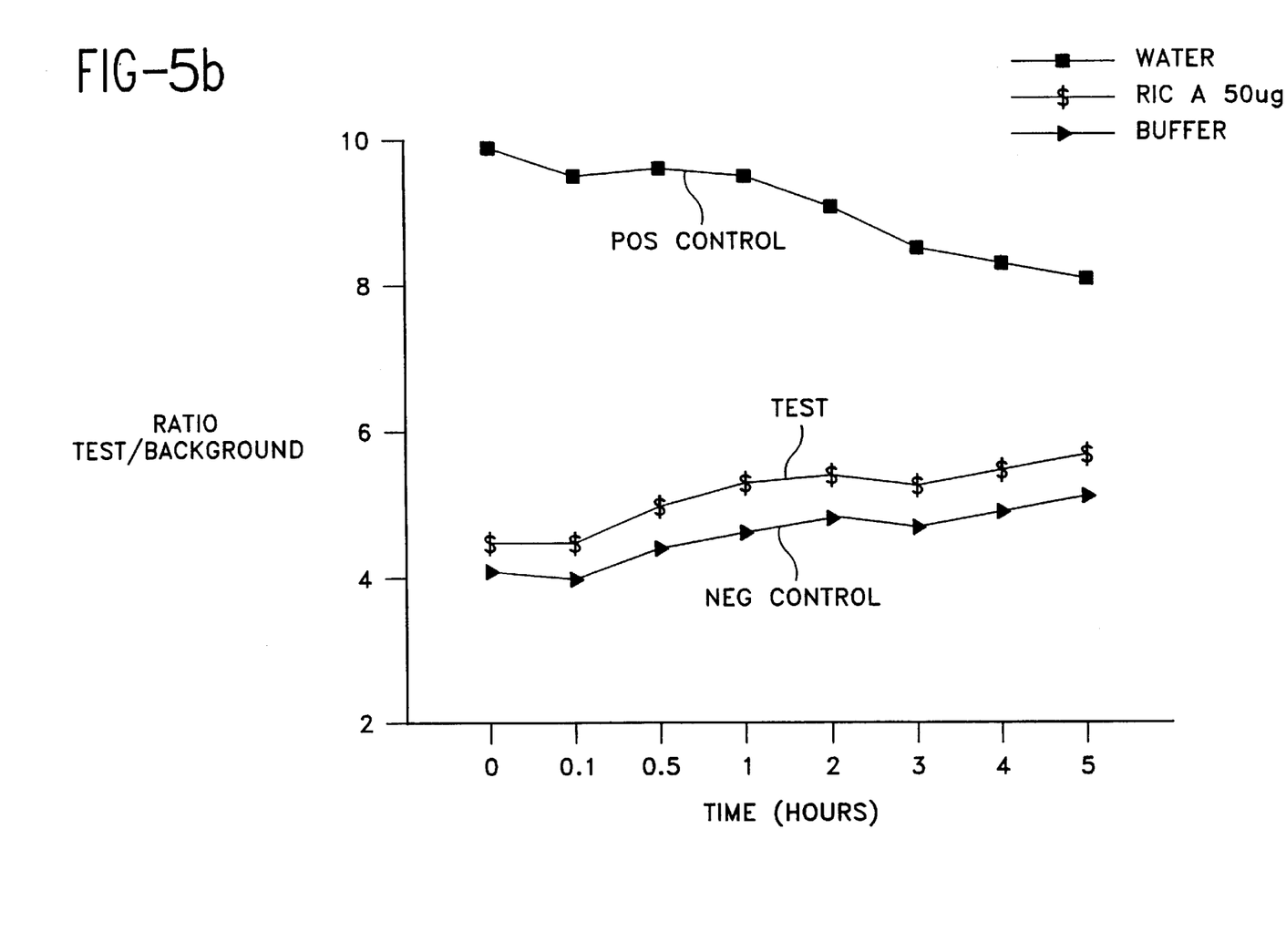
FIG. 5b is a graph illustrating fluorescence uptake by *E. coli* in the presence of Ricin A chain using a process in accordance with the present invention.

Ricin A chain is the active component of the total ricin molecule and has been shown to be highly toxic. Ricin A chain was also diluted in buffer and tested. The results are shown in FIG. 5b. As seen, Ricin A chain demonstrated a significant increase in SYTOX uptake over the buffer control.

3.7 Small 25–35 mer Polypeptide Neurotoxins

Figure 6:
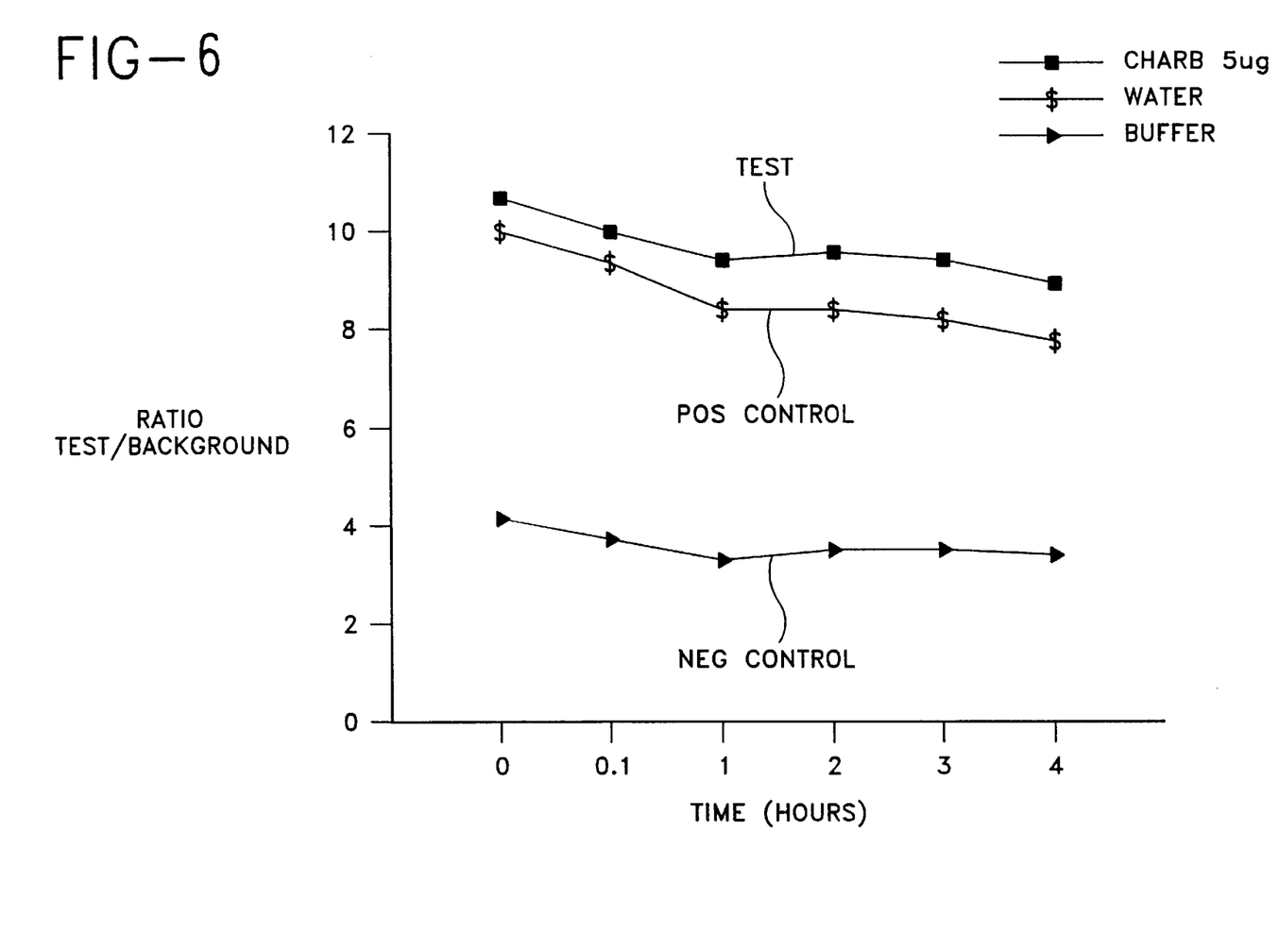
FIG. 6 is a graph illustrating fluorescence uptake by *E. coli* in the presence of charybdotoxin using a process in accordance with the present invention.
Figure 7:
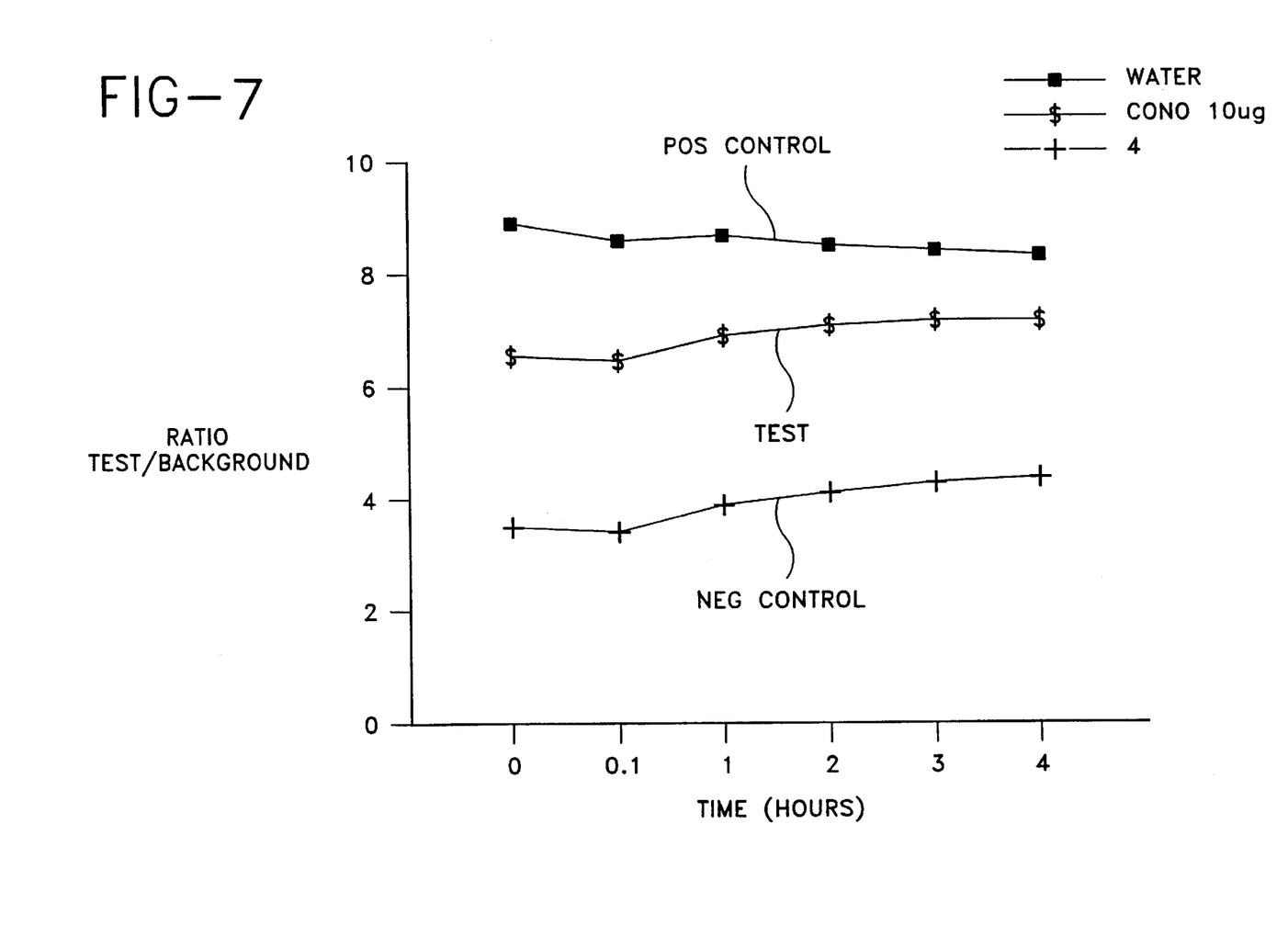
FIG. 7 is a graph illustrating fluorescence uptake by *E. coli* in the presence of conotoxin GVIA using a process in accordance with the present invention.
Figure 8:
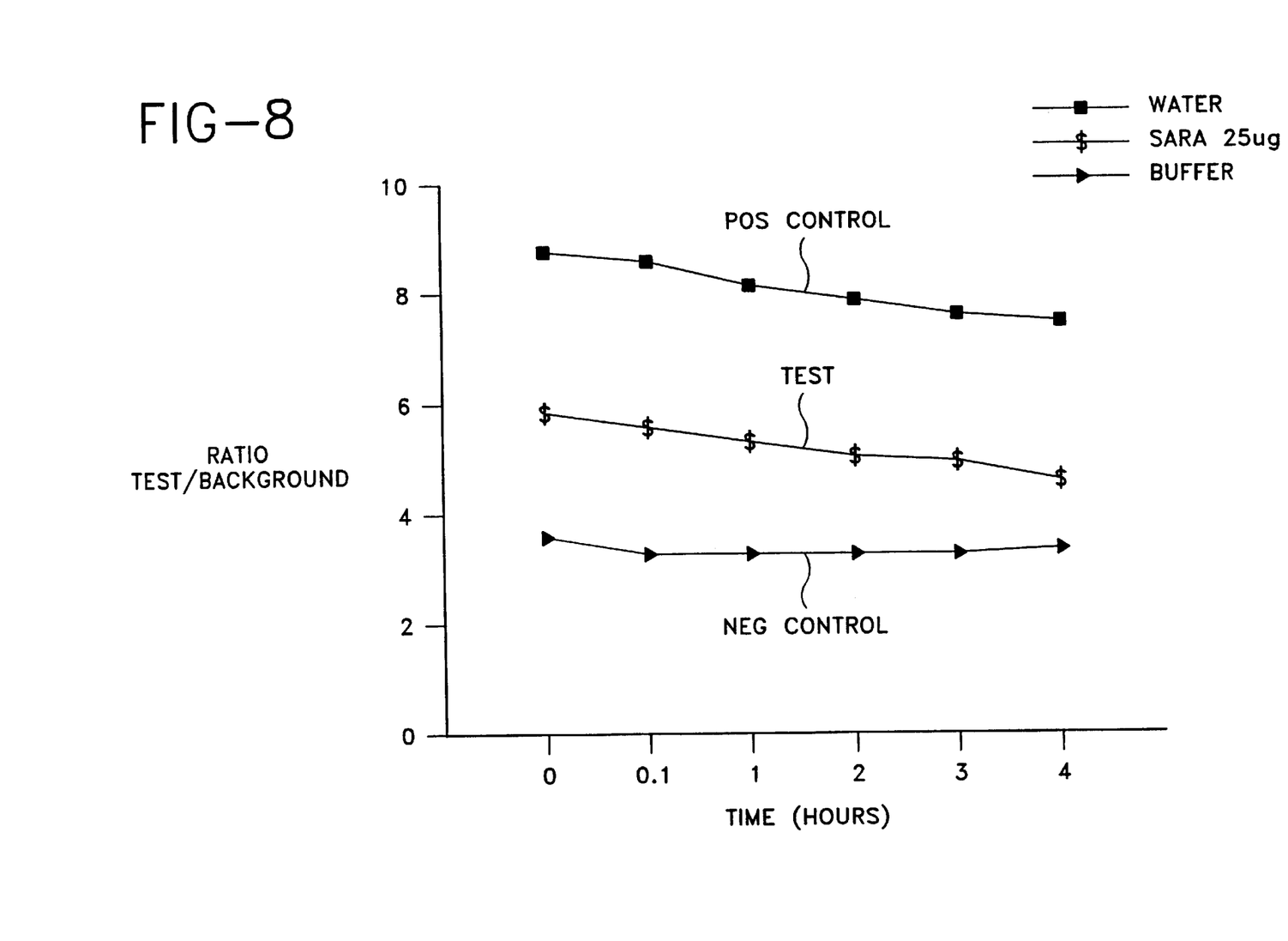
FIG. 8 is a graph illustrating fluorescence uptake by *E. coli* in the presence of sarafotoxin using a process in accordance with the present invention.

Since cecropins functioned by permealizing the membranes of bacteria, it became of interest to determine if toxic polypeptides would also produce the same effect detectable by an increase in SYTOX uptake in the test bacteria. Charybdotoxin, conotoxin GVIA, and sarafoxtoxin were dissolved in buffer and tested as described. The results show that charybdotoxin (FIG. 6), conotoxin (FIG. 7) and sarafotoxin (FIG. 8) all were positive in this test system with a significant increase in SYTOX uptake over controls.

CONCLUSIONS

This system has proven in the laboratory to be a rapid system for the detection of membrane damaging or membrane traversing toxins. It has been shown to be capable of the instantaneous detection of a wide variety of toxins with various molecular weights and different modes of action in humans. It is simple to set up with a minimum of equipment and training and should be able to be adapted to field use for the rapid detection of toxins which would allow rapid anti-biological defense measures to be instituted.

In addition to military uses, this technology could also be adapted for use in the civilian industrial/pharmaceutical industries. This detection system could be installed in manufacturing and/or storage facilities where toxins or toxic materials are being produced or stored for legitimate industrial or medical research purposes. Positive detection of a released toxin would give an early warning that the safety procedures already in place have been breached and rapid evacuation of personnel in the area could be initiated.

While the invention has been described in connection with preferred embodiments, it will be understood that it is not intended to limit the invention to those embodiments. On the contrary, it is intended to cover all alternatives, modifications and/or equivalents as may be included within the spirit and scope of the invention defined in the appended claims.

What is claimed is:

1. A method of detecting the presence of toxins in test samples, which comprises:
   (a) obtaining a negative control fluorescent signal by placing a live indicator bacteria in a buffer containing a fluorescent marker which is of the type which fluoresces only upon binding to bacterial DNA;
   (b) obtaining a test fluorescent signal by combining in a separate vessel a test sample for which the pessence of toxin is unknown, said live indicator bacteria, and said fluorescent marker which is of the type which fluoresces only upon binding to bacterial DNA in said buffer, said signal being generated instantaneously; and
   (c) comparing the signal generated by said test sample to the signal obtained for said negative control, whereby the presence of a toxin in said test sample is indicated when said test sample fluorescent signal is greater than the negative control sample fluorescent signal.

2. The method of claim 1, wherein said live indicator bacteria is *Escherichia coli*.

3. The method of claim 2, wherein said *Escherichia coli* is *Escherichia coli* K-12.

4. The method of claim 3, wherein said *Escherichia coli* K-12 is selected from strains consisting of LE392, Y1083, JM109, MC1061 and C600.

5. The method of claim 1, wherein said live indicator bacteria is a cecropin sensitive bacteria.

6. The method of claim 1, further comprising;
   first obtaining a positive fluorescent control signal by placing said live indicator bacteria and a bactericidal peptide in said buffer containing said fluorescent marker which fluoresces only upon binding to bacterial DNA.

7. The method of claim 6, wherein said bactericidal peptide is a cecropin.

8. The method of claim 1, wherein said fluorescent marker is SYTOX.

9. The method of claim 1, wherein the toxin detected is selected from the group consisting of *Escherichia coli* heat-labile enterotoxin, *Escherichia coli* heat stable enterotoxin, cholera toxin, adenylate cyclase activating polypeptide, staphylococcal enterotoxin, Ricin A chain, conotoxin, charybdotoxirin and sarafotoxin.

10. The method of claim 1, wherein the fluorescent signal generated by said marker is quantified using a fluorescence measurement system having an excitation filter of about 485+/−20 nanometer wavelength and an ermission filter of about 530+/−25 nanometer wavelength.

11. A method of detecting the presence of bacteria in a test sample, which comprises:
    (a) obtaining a negative control signal by placing a live indicator bacteria in a buffer containing a fluorescent marker which is of the type which fluoresces only upon binding to bacterial DNA;
    (b) obtaining a test signal by combining in a separate vessel a test sample for which the presence of bacteria is unknown, a buffer containing a fluorescent marker which is of the type which fluoresces only upon binding to bacterial DNA, and a bactericidal peptide, said signal being generated instantaneously; and
    (c) comparing the signal generated by said test sample to that obtained for said negative control;
    whereby the presence of bacteria in the test sample is indicated when the fluorescent signal of said test sample is greater than that of said negative control.

12. The method of claim 11, wherein said indicator bacteria is *Escherichia coli*.

13. The method of claim 12, wherein said *Escherichia coli* K-12 is selected from strains consisting of LE392, Y1083, JM109, MC1061 and C600.

14. The method of claim 11, wherein said *Escherichia coli* is *Escherichia coli* K-12.

15. The method of claim 11, further comprising:
    obtaining a positive control fluorescent signal by combining said live indicator bacteria, said fluorescent marker for bacterial DNA, and said bactericidal peptide in a solution buffered to a substantially neutral pH.

16. The method of claim 11, wherein said fluorescent marker is SYTOX.

17. The method of claim 11, wherein the bacteria detected is selected from the group consisting of non-toxin A producing *Vibrio cholera, Pseudomonas aerugenosa*, and *Escherichia coli* other than K-12.

18. A kit for detecting the presence of toxins or bacteria in an environmental sample, which comprises a sufficient amount of:
    (a) an indicator bacteria strain;
    (b) a fluorescent marker for bacterial DNA;
    (c) a bactericidal peptide; and
    (d) vessels for containing a positive control fluorescent signal mixture; a negative control fluorescent signal mixture, and a plurality of environmental sample signal mixtures.

19. The kit of claim 18, further including a fluorescence measurement apparatus.

* * * * *